US 6,416,522 B1
United States Patent
Strecker
(10) Patent No.: US 6,416,522 B1
(45) Date of Patent: Jul. 9, 2002

(54) INTRALUMINAL IMPLANTATION DEVICE

(76) Inventor: Ernst Peter Strecker, Vierordtstrasse 7A, D-76228 Karlsruhe (DE)

( * ) Notice: Subject to any disclaimer, the term of this patent is extended or adjusted under 35 U.S.C. 154(b) by 0 days.

(21) Appl. No.: 09/463,350

(22) PCT Filed: Jul. 23, 1998

(86) PCT No.: PCT/DE98/02136

§ 371 (c)(1),
(2), (4) Date: Jan. 24, 2000

(87) PCT Pub. No.: WO99/04724

PCT Pub. Date: Feb. 4, 1999

(30) Foreign Application Priority Data

Jul. 24, 1997 (DE) .......................... 197 31 834

(51) Int. Cl.[7] .............................. A61B 17/10
(52) U.S. Cl. ................. 606/143; 623/1.23; 623/1.11
(58) Field of Search .................. 623/1.23, 1.11; 606/159, 143; 227/175.1–175.6; 604/532

(56) References Cited

U.S. PATENT DOCUMENTS

| 4,872,874 | A | | 10/1989 | Taheri | |
|---|---|---|---|---|---|
| 5,042,707 | A | * | 8/1991 | Taheri | .................. 606/213 |
| 5,254,127 | A | | 10/1993 | Wholey et al. | |
| 5,282,829 | A | * | 2/1994 | Hermes | .................. 606/219 |
| 5,395,030 | A | * | 3/1995 | Kuramoto et al. | .......... 227/179 |
| 5,843,169 | A | * | 12/1998 | Taheri | ............................ 623/1 |

FOREIGN PATENT DOCUMENTS

| EP | 0 380 666 | 8/1990 |
|---|---|---|
| EP | 0 466 518 | 1/1992 |
| WO | WO90/15582 | 12/1990 |

* cited by examiner

*Primary Examiner*—Corrine McDermott
*Assistant Examiner*—Thomas C. Barrett
(74) *Attorney, Agent, or Firm*—Collard & Roe, P.C.

(57) ABSTRACT

The implantation device for treating damaged or diseased tissue within the region of the walls of hollow organs comprises a catheter and at least one securing means detachably received in a receptacle of the catheter. After the catheter has been placed in its appropriate position in the hollow organ, said securing means is implantable in the wall of the hollow organ with a. least one implantation segment of said means. The catheter may be provided with means for receiving a protective cover for covering larger diseased areas of the tissue, as well as with means for tensioning the hollow organ prior to and in the course of the implantation process. The securing means are nails, staples, screws or spirals having a length adapted to the thickness of the wall of the hollow organ to be treated. Such securing means are implanted in the vascular wall with the help of an element of the catheter, for example a pusher axially movably received in the catheter.

37 Claims, 8 Drawing Sheets

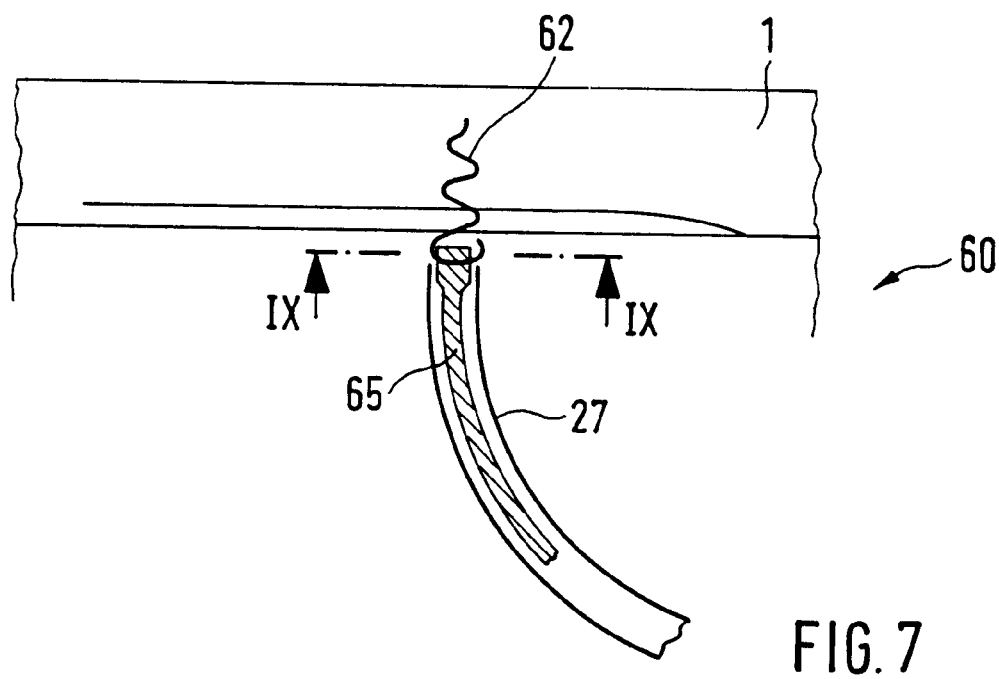
FIG. 7
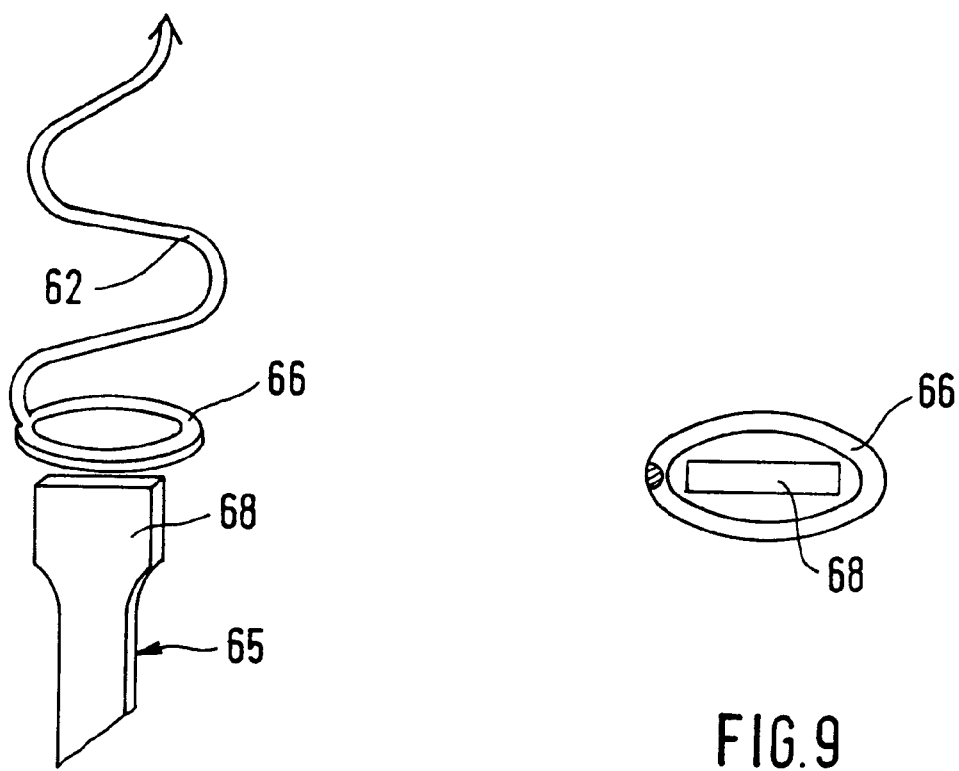
FIG. 8
FIG. 9

INTRALUMINAL IMPLANTATION DEVICE

The invention relates to an implantation device for treating damaged or diseased tissue in the region of the inner walls of hollow organs, and in particular to an implantation device for treating a dissection in body vessels, with a catheter and at least one fastening means connected with said catheter, whereby the catheter has a long-stretching hollow body which is open at least at its front end when employed as intended, and in which each fastening means is received with axial mobility when the implantation device is inserted in the vessel of the body.

Such an implantation device is known from EP-A-466 518 even though said device is not intended for treating vessels of the body.

Said known implantation device is a device for implanting an artificial blood vessel, which is implanted by means of a catheter in the correct position and expanded in the site of implantation. For this purpose, the artificial blood vessel is received during the implantation in a constricting covering, which is removed after the implantation. The artificial blood vessel is provided with spring elements which, in turn have barbs that get hooked up in the site of implantation, and in this way maintain the artificial blood vessel elastically in its desired position, expanding it to some extent as desired. Owing to the fact that the elastic fastening means are connected with the artificial blood vessel and, to that extent, in each case indirectly also with the catheter, exact positioning of the fastening means as deemed desirable, for example for treating dissections, but also in connection with other applications, is not possible. In connection with the object of EP-A-466 518, the fastening means are rather connected with the artificial blood vessel in a fixed manner. Therefore, it is not possible with said known implantation device to implant the fastening means as such.

A method and a device for securing a graft in the lumen of a body vessel are known from U.S. Pat. Ser. No. 4,872, 874. The known device comprises a catheter with an expandable balloon segment at its distal end. The balloon segment is provided with a U-shaped annular groove, in which staples as securing means are distributed over the circumference and receivable with legs connected with each other via a bridge in such a way that the free ends of the legs point outwardly. By means of said device, a graft first introduced in a body vessel can be secured on vascular walls by positioning the balloon segment with the annular groove receiving the securing means, said balloon segment being inserted in the vessel in its expanded condition and being provided with securing means, within the proximity of one end of the graft, and by subsequently inflating the balloon segment. In this process, the radially protruding legs of the staples have to pierce the graft and penetrate the vascular wall in order to keep the graft attached to the vascular wall after the balloon segment has been deflated.

However, it has been found that the legs of the staples serving as securing means easily assume a slanted position when the balloon segment is expanded, or only inadequately penetrate the vascular wall. This can be assumed to be attributable to the fact that the depth of the annular groove serving for receiving the securing means becomes progressively smaller, causing the securing means to lose their guidance. As a result thereof, the graft is only inadequately tacked to the vascular wall, and, furthermore, damage may be caused to the vascular wall.

In the known device, the balloon segment of the catheter is considerably widened radially even when it is in its unexpanded condition, so that this implantation device can be employed on with larger body vessels.

Accordingly, the invention is based on the problem of creating an improved implantation device of the type and for the purpose specified above. Such device permits strictly local treatments of damaged or diseased tissue of the inner walls of hollow organs while reducing at the same time the stress to which the tissue is subjected to in such treatments.

Said problem is solved in that the implantation device as defined in the introductory part of claim 1 comprises a catheter with a long-stretched hollow body, which is open at least at its front end when used as intended, and in which one or a plurality of securing means are received with axial mobility. The application of such a catheter requires only a small cross section for its insertion. Such a catheter is, therefore, suitable also for vessels with a small lumen. After the catheter has been placed in its correct position, the securing means received therein is expelled from the catheter and implanted in the vascular wall.

The implantation device thus comprises a catheter in which one or several securing means are received when it is introduced in the body vessel. Following placement of the catheter in its appropriate position within the region of the site of the diseased tissue, for example on a dissecate, said securing means are advanced from the catheter and implanted in the vascular wall. In case of a dissecate, the treatment is carried out in a simple fashion in that the dissecate is tacked to the vascular wall with the help of the securing means. The implantation device as defined by the invention therefore assures that the treatment of the dissecate is precisely "on target". The tissue is stressed only within the immediate proximity of the securing means and the stress to which the tissue of the organ is subjected to is consequently reduced to a minimum. With larger dissecates, the application of several securing means is recommended, which have to be implanted spaced from each other.

The possibilities available for employing the implantation device as defined by the invention extend far beyond the treatment of vascular diseases and may comprise also, for example the treatment of detachments of the retina, by reliably and permanently connecting the latter with the choroid with the help of securing means. As opposed to currently applied coagulation therapies, which only permit a prophylactic treatment of endangered regions, the treatment with the help of the implantation device as defined by the invention also permits reattachment by tacking on areas of the retina that have become detached.

Treatment possibilities are expanded in that means for receiving and positioning a protective cover for the affected tissue are arranged on the catheter. It is possible with the help of the protective cover to treat also large areas of the tissue regions, where the use of only securing means is inadequate or not possible. Covering the bag-like dilatation of the vessel with such a protective cover is recommended especially for the treatment of aneurisms, whereby the protective cover is tacked within the marginal region of the aneurism with securing means in the healthy tissue. As opposed to the conventional treatment with stents, the lumen of the vessel is not narrowed down and the risk of a stenosis due to formation of a neointima is largely reduced.

The type of protective covering to be used depends in this connection on the application in a given case. A useful protective covering is, for example a piece of textile or tissue adapted to the damaged area of the tissue. The fabric may consist of a stable or flexible material depending on the application. The use of a biodegradable material is recommendable for many applications. In particular, the use of the body's own tissue or of a transplant is possible as well.

The present implantation device also permits tacking grafts to the inner wall of a body vessel. A supporting stent structure can be entirely omitted in this way. As opposed to conventional treatments with stents, the lumen of the body vessel is not noticeably reduced.

A nail adapted to the thickness of the wall of the hollow organ is a securing means that is adequate in many cases. The shaft of such a nail is inserted in the vascular wall. However, staples with two or more legs can be used as well depending on to which extent the affected region of the tissue is stressed, with the legs of such staples being arranged U- or V-shaped relative to each other. Also, the securing means may have two flexible legs, which are connected with each other with one of their ends. In the course of the implantation process, said legs are kept parallel with each other in the catheter and spread in the form of a "V" only as the catheter is being implanted, which keeps the cross section being used in the course of insertion of the catheter very small, on the one hand, and produces a reliable and fixed connection in the state of implantation on the other. Furthermore, the securing means can be fitted with barbs, which further increases the strength of the connection provided by the securing means.

It is very advantageous as well from case to case if a biodegradable material is used also for the securing means. If the securing means consist of an elastic material such as, for example, "Nitinol", the introduction of the catheter segment containing the securing means is facilitated if the body vessels are highly curved, and the risk of damage is reduced.

As an alternative to securing means consisting of solid materials, it is possible also to employ a material that is liquid in the course of implantation and squeezed out of the catheter, and hardens or cures in the implantation site after a certain period of time.

So that the treatment can be monitored in an optimal way, it is useful if the securing means is marked with diagnostic contrast media in order to facilitate monitoring of the surgical intervention, for example with the help of X-radiation or magnetic resonance. In order to avoid interference with the imaging in magnetic resonance tomography, a metal should be used in this connection that is not active ferromagnetically.

According to another advantageous development of the invention the securing means is suitable for receiving and dispensing a predetermined amount of medication in a controlled manner. This reliably assures that an optimal medicinal supply is available for locally limited damaged areas, for example in the treatment of ulcers or the like.

For receiving medications it is possible to consider, for example hollow spaces arranged in the securing means itself, which are either provided with apertures from which the medication exits in a controlled way, or which, when a biodegradable material is used, release the medication in the course of the degradation process of the securing means. Particularly when medications have to be used in greater amounts, it is useful if a medication pouch is attached with the help of the securing means within the immediate proximity of the diseased region. The medication pouch, which preferably consists of a biodegradable material, may have small apertures from which the medication exits at a predetermined release rate.

In order to facilitate the implantation of the securing means, the hollow body of the catheter is advantageously bent upwardly with its front end. Such upwardly bent configuration also effect an entirely desirable limited expansion of the body vessel in the course of implantation.

In another embodiment, the hollow body consists of an elastic material, so that such body is present in the longstretched state as the catheter is being introduced in the body vessel, and its front segment is bent up in the direction of the vascular wall only after it has been placed in the vessel in its correct position. It is important in this connection that the inside cross section of the hollow body remains substantially the same as it is being bent in order to avoid that the securing means is canted in the hollow body, or not implanted in the body vessel in the intended way.

A simple yet effective possibility for implanting the securing means in the intended manner in the wall of the hollow organ is to receive a pusher with axial mobility in the hollow body of the catheter. When employed as intended, such pusher can be actuated at the proximal end of the catheter. At its front end, the pusher is actively connected with the securing means in such a way that that the securing means can be pushed out of the catheter with the help of the pusher and implanted in the wall of the organ.

In yet another embodiment of the invention, the securing means is designed in the form of a screw or spiral and has a coupling means on its rear segment for connecting it with torsional strength yet detachably with a corresponding coupling segment of the pusher. With such an embodiment, implantation is carried out as follows: after the catheter has been placed in its correct position, the securing means is screwed into the wall of the organ by actuating the pusher as required, and then detached from the pusher after it has been implanted.

According to another advantageous development of the invention, the hollow body of the catheter is received in a sleeve with at least part of its longitudinal expanse. The sleeve serves in this connection for the protection of the hollow body and, if the latter consists of a particularly flexible material, for stabilizing the catheter as it is being introduced in the hollow organ.

With catheters having a flexible hollow body, the front segment of the hollow body can be bent or deflected upwardly in a simple manner by a filament which, in its intended state, extends along the catheter and has its front end connected with the hollow body. The catheter, except for a predetermined front segment thereof, is stiffened by suitable means, for example by the aforementioned sleeve, so that only said front segment can be deflected or bent upwardly by actuating the filament.

In yet another embodiment, the filament extends in the interior of the hollow body in a second lumen in the wall of the catheter. In this embodiments the front segment is deflected upwardly in the way of a Bowden wire. Also, the filament may consist of a wire, in which case superior stability is obtained.

So that damage to the catheter and also to the vascular wall is avoided to the greatest possible extent, the segment to be deflected is provided with a reinforcement according to claim 25. Such reinforcement may be, for example a thin, flexible metal foil, which is arranged in this part of the hollow body of the catheter. Furthermore, the catheter may be completely made of metal such as, for example, "Nitinol".

In yet another embodiment, the securing means is actively connected with spring means, with whose help the securing means is inserted at high speed in the wall of the hollow organ and produces there a particularly reliable and solid connection, for example on a dissecate on the vascular wall. The spring means may be arranged within the hollow organ in the catheter and may be directly connected with the securing means. When the catheter is introduced in the hollow organ, the spring means are pretensioned, and are released by a suitable releasing device after the catheter has been placed in its appropriate position. This can be accomplished, for example by means of a pusher, which is guided through the hollow body of the catheter. It is possible also to mount the spring means at the proximal end of the catheter, thus outside of the body, and to transmit the spring forces to the securing means with the help of the pusher.

Instead of employing spring means it is possible also to use an electromagnetic drive, which is arranged outside of the body and which advances the securing means via the pusher over a predetermined distance. According to another alternative, provision is made that the securing means is driven into the wall of the hollow organ by means of ultrasonic waves, which are emitted by an ultrasound arrangement actively connected with the lumen of the hollow body of the catheter.

Usefully, several simultaneously implantable securing means are received in the hollow body. This is particularly advantageous when securing larger protective coverings or a hose-like graft.

According to yet another development of the invention, several securing means are arranged in associated receiving segments of the front part of the hollow body of the catheter. After the catheter has been appropriately positioned in the hollow organ, the various receiving segments are bent up independently of each other in the direction of the intended site of implantation and the securing means are subsequently driven in, preferably simultaneously.

So as to assure a rational and careful intervention, provision is made according to claim 31 for arranging a plurality of securing means one after the other in the hollow body of the catheter, so that a sequential implantation can be carried out This design is very advantageous particularly for the treatment of long-stretched dissecates.

According to another embodiment of the implantation device as defined by the invention, provision is made that a magazine with a plurality of securing means and a loading device are arranged on the catheter. After each implantation of a securing means, the loading device takes another securing means from the magazine and positions it in the site in the hollow body which was previously occupied by the now-implanted securing means. It is possible in this way to implant a great number of securing means in the course of one single intervention.

Alternatively to the magazine, provision is made according to claim 33 for elastically stretchable securing means, which are received laterally of the pusher in the hollow body of the catheter and/or in the sleeve of the catheter, and which, after a first securing means has been implanted, are pushed into the starting position of the implanted securing means with the help of suitable means, for example a loading pusher extending coaxially around the pusher, whereby such securing means automatically change into the intended form of implantation.

In yet another embodiment, the hollow body of the catheter is in connection with a feed hose, through which further securing means can be pushed in the hollow body of the catheter with the help of a separate feeding pusher. It is particularly advantageous in this connection that basically any desired number of securing means can be inserted without having to remove the catheter from the body vessel. However, in a similar way even the hollow body of the catheter itself can be employed as a feeding hose.

So as to achieve a satisfactory success of the treatment it is important that the tissue intended for implantation with a securing means is under pretension at the time of the surgical intervention. In the exemplified embodiment according to patent claims 14 to 34, such pretension is assured especially by the unbent front segment of the hollow body. In order to enhance the pretension, provision is made according to claims 35 and 36 for additional devices arranged on the catheter. The object according to claim 35 is a spreading sleeve consisting of bridges separated from each other by longitudinal slits. The spreading sleeve is inserted in the vessel with the catheter in the stretched condition, in which the bridges are arranged resting substantially parallel against each other. After the catheter has been placed in the correct position, the spreading sleeve is spread by means of a suitable pulling element in order to provide the vessel with the desired pretension. After the implantation is completed, the spreading sleeve is again changed into the stretched condition and removed from the vessel. According to claim 36, the catheter is actively connected with a balloon catheter which, after its expansion, also effects a uniform expansion of the entire vessel section. The implantation catheter extends partly within the spreading sleeve or the balloon catheter and is brought there into its intended position. In the case of the balloon catheter, implantation of the securing means can take place, for example through a predetermined opening in the sleeve of the balloon catheter.

In order to prevent the point or tip of the catheter or the securing means from sliding down on the wall of the hollow organ, provision is made according,to claim 37 that the front end of the catheter is pointed and, after the catheter has been placed in the right position, slightly penetrates the vascular wall, which substantially reduced the risk of letting it slide down.

If provision is made for means for receiving a protective covering on the catheter, it is particularly advantageous if such means can be controlled independently of each other, for example by means of suitable positioning wires. This permits positioning of the protective covering in the intended site with great accuracy.

If possible, the positioning wires should be arranged within separate channels in the wall of the catheter.

In yet another embodiment, the catheter has a probe made of a thin filament, on which a securing means designed at least in sections in the form of a hollow element is detachably received when the implantation device is in its inserted state. Such a design is especially useful with very narrow vessel cross sections. Such a probe, too, can be deflected upwardly with its front segment by means of a filament mounted on the probe, so that the securing means can be brought into a starting position preferred for its implantation. The catheter itself, which extends coaxially around the probe, serves in this connection for inserting the securing means in the vascular wall.

In another advantageous development of the invention, the implantation device is equipped with an ultrasound probe arranged on the catheter for image acquisition, such probe permitting direct monitoring of the region of the surgery.

A number of exemplified embodiments of the invention are explained in the following in greater detail with the help of the drawings, in which:

FIG. 7 shows another embodiment of the front segment of an implantation device, with a securing means wound in the form of a spiral.

FIG. 8 shows the securing means of FIG. 7 and a pusher by an enlarged exploded representation.

FIG. 9 shows an enlarged cross sectional view of the coupling of the securing means and of the pusher, with a cut along section line IX—IX in FIG. 7.

Figure 1:
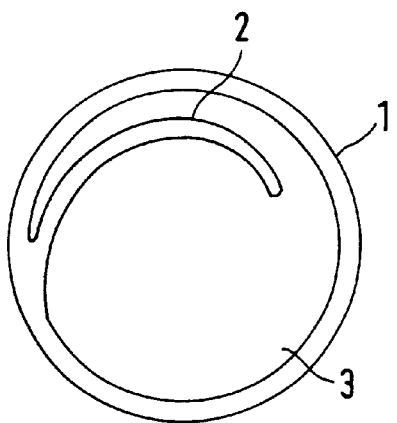
FIG. 1 shows a cross section through a body vessel with a dissecate.
Figure 2:
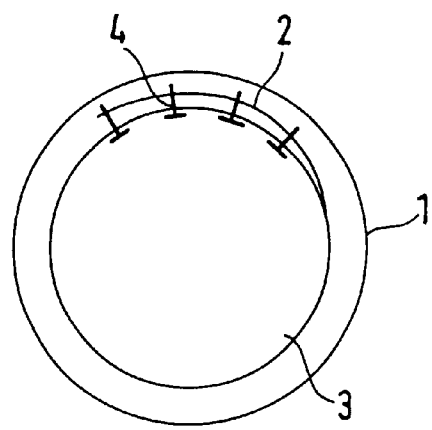
FIG. 2 shows a dissecate applied to the wall of the vessel with securing means.

Body vessel 1 shown in FIG. 1 has a so-called dissecate 2, thus a tissue portion partly projecting into lumen 3 of body vessel 1. Such dissecates develop frequently after a preceding angioplastic treatment of body vessels by means of balloon catheters. In the treatment of dissecate 2 with the implantation device as defined by the invention, dissecate 2 is pressed against the inner wall of body vessel 1 and tacked to the wall of body vessel 1 with the help of one or a plurality of securing means 4.

Figure 3:
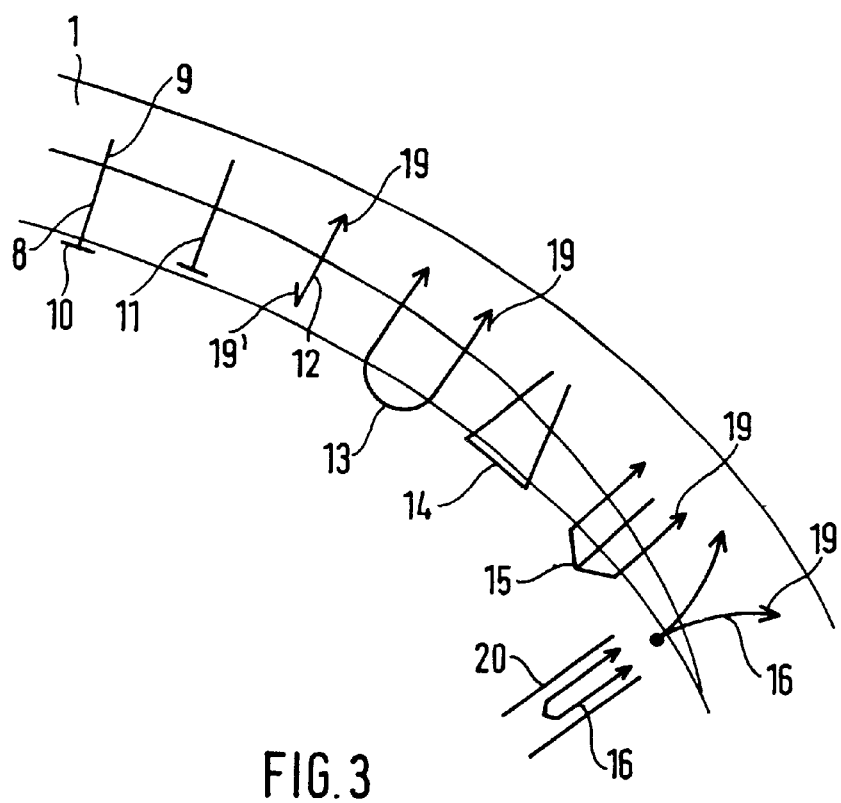
FIG. 3 shows an enlarged cutout view of different securing means.

FIG. 3 shows various securing means 8 and 11 to 16 in their intended implanted state in the wall of a body vessel 1. A nail 8 represents a simple securing means which, however, suffices in most cases. Shaft 9 of said nail has a length adapted to the vascular wall. So as to prevent any stenoses from developing on nail head 10 projecting from the vascular wall, it is useful if nail 10 is driven during implantation into the wall of vessel 1 to such an extent that the head of the nail no longer projects into the lumen of body vessel 1, as shown on the example of nail 11. Nail 11 is covered after a certain time by vascular tissue also at its head end and thus no longer represents any source of danger in view of possible stenoses.

For producing a particularly solid connection, nail 12 has barbs 19, 19' both on its shaft point and its head part. The securing means also may be designed in the form of staples for different applications. Staple 13 is provided with legs bent U-shaped relative to each other, and staple 14 has two legs mounted on a bridge extending in the intended condition parallel with the inner wall of body vessel 1, said legs being inclined toward one another. A particularly solid connection is produced by the three-legged staple 15 which, like staple 13 bent in the shape of a "U", may be additionally fitted with barbs 19.

Staple 16, which is provided with two elastic legs, represents a particularly useful securing means: when a catheter 20 is inserted, said legs are received in the hollow body of the catheter, whereby the legs of staple 16 are disposed close to each other. During implantation, i.e., when staple 16 is driven out of catheter 20 and penetrates the vascular wall, the two legs spread for changing into the intended implantation condition of staple 16.

Figure 4:
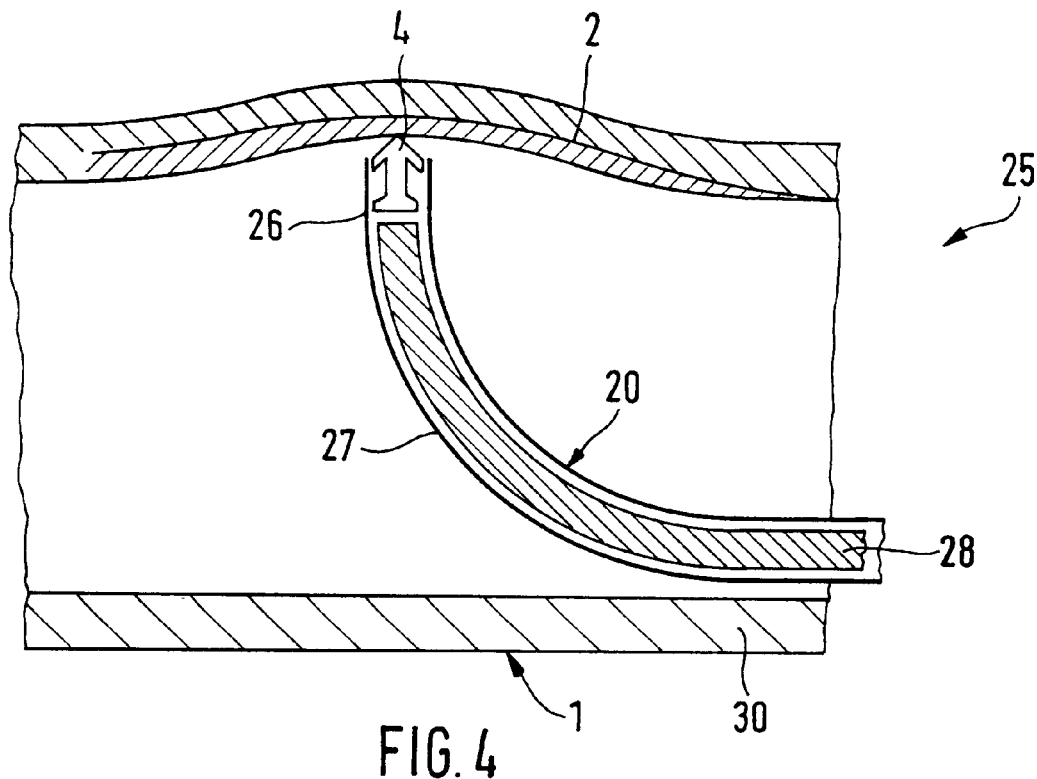
FIG. 4 shows a longitudinal sectional view of the front segment of a catheter of an implantation device inserted in a vessel.

FIG. 4 shows an implantation device 25 in its intended condition for treating a dissecate 2 in the wall of a body vessel 1. Implantation device 25 consists of a catheter 20 and a securing means 4. Catheter 20 has a long-stretched hollow body 27, which is open at its distal end 26, as well as a pusher 28, the latter being guided through said hollow body and being actively connected with securing means 4. Hollow body 27 is bent upwardly with its front segment in such a way that the distal end 26 of hollow body 27 is substantially arranged perpendicular to the longitudinal axis of body vessel 1. Supporting itself on a wall section 30 of body vessel 1, hollow body 27 presses with its distal end 26 against the wall of body vessel 1 within the range of dissecate 2 and thereby keeps vessel 1 under pretension, which is advantageous to the implantation process, Securing means 4 is implanted after catheter 20 has been placed in the correct position by advancing pusher 28 in hollow body 27.

Figure 5:
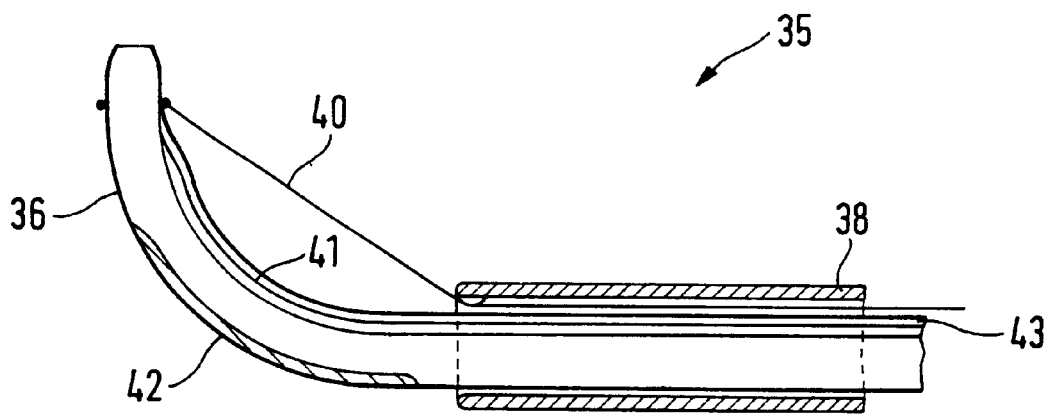
FIG. 5 shows a longitudinal section through the front segment of a catheter of an implantation device of another design.

While catheter 20 according to FIG. 4 has a substantially elastic hollow body and is inserted in a stretched condition with the help of a guiding wire not shown here, yet automatically raises itself to assume the intended curved shape after it has been placed in the correct position in the body vessel, catheter 35 shown in FIG. 5 has a hollow body 36 made of a flexible material.

For stabilizing hollow body 36 in the course of insertion of catheter 35 in a body vessel 1, hollow body 36 is surrounded by a sleeve 38 across the major part of its longitudinal expanse. At its distal end, hollow body 36 is connected with a filament 40, with the help of which the front segment of hollow body 36 is bent up for the purpose of assuming the intended implantation position. Like hollow body 36, filament 40 is received in sleeve 38 with axial mobility. After catheter 35 has been inserted in a body vessel, the sleeve is retracted by a predetermined distance from the distal end of hollow body 36 in order to clear a front segment of hollow body 36 for bending such segment up with the help of filament 40, such front segment being suitable for the given application. A reinforcement 42 prevents the securing means and/or the pusher from penetrating the wall of hollow body 36 when being advanced in the latter. Instead of using the filament 40 arranged on the outside on hollow body 36 within sleeve 38, it is possible also to use a filament 41 extending on the inside in hollow body 36 in a separate lumen 43, such filament also being fastened on the front segment of hollow body 36 and bending the latter upwardly into its intended position in the way of a Bowden wire.

Figure 6A:
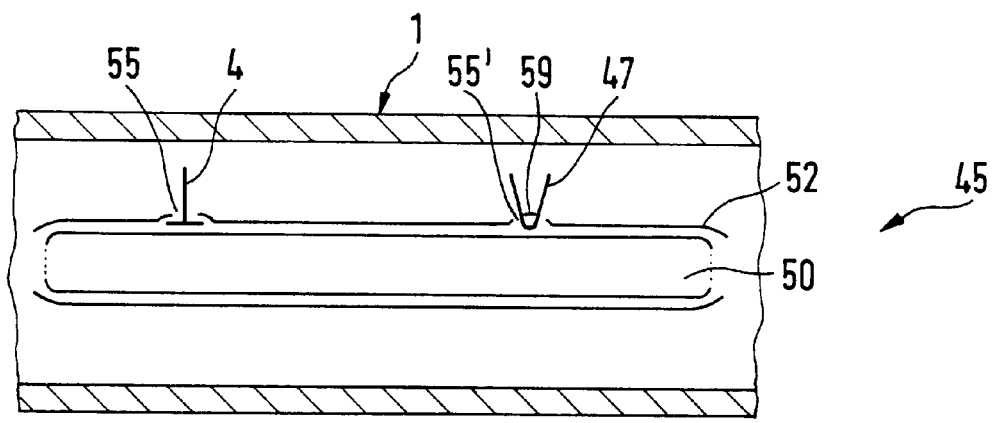
FIG. 6a shows an unexpanded balloon catheter inserted in a vessel (only indicated), with a sleeve received on said catheter and holding securing means.
Figure 6B:
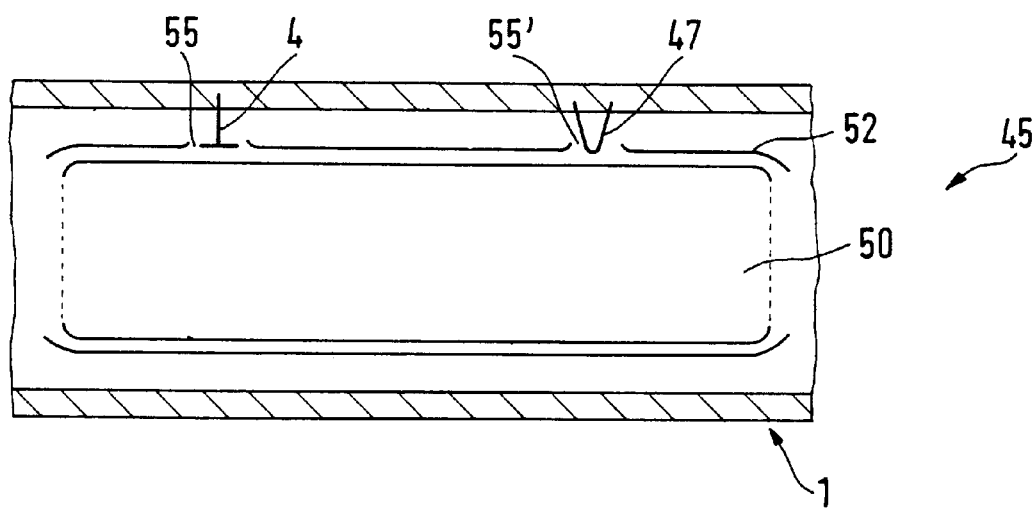
FIG. 6b shows a view of the balloon catheter as shown in FIG. 6a, with a sleeve in the widened condition received on said catheter.

FIGS. 6a and 6b show another design of an implantation device 45 as defined by the invention. In this embodiment, the securing means 4, 47 are arranged radially on the outside on the outer wall of a balloon catheter 50. Balloon catheter 50 is enclosed by a flexible sleeve 52. With their implantation segments facing the wall of body vessel 1, securing means 4, 47 each penetrate the openings 55, 55' arranged in sleeve 52. In the unexpanded (deflated) condition of balloon catheter 50, which is shown in FIG. 6a, the cross section of sleeve opening 55 is smaller than the cross section of securing means 4, which is designed in the form of a nail. Securing means 4 is therefore radially solidly held on the balloon catheter by the sleeve. Securing means 47, which is designed in the form of a staple, is also radially solidly held on balloon catheter 50 by a bridge-like holding filament 59 of sleeve 52. In the expanded (inflated) condition of balloon catheter 50, which is shown in FIG. 6b, sleeve opening 55 is widened in such a way that securing means 4 is released also with its head. At the same time, securing means 4 is driven with its implantation segment into the wall of body vessel 1 due to the expansion of balloon catheter 50. Furthermore, as balloon catheter 50 expands, the bridge-like holding filament 59, which held securing means 47 as the catheter was being inserted, is torn, and securing means 47 is thus released as well, the latter being implanted in the wall of body vessel 1 in basically the same way as securing means 4. After the implantation is completed, the balloon catheter is changed to its insertion condition (with a small cross section) and removed again from the body vessel.

FIGS. 7 to 9 show an implantation device 60 of yet another design with a securing means 62 wound in the form of a spiral. A particularly reliable and durable connection can be produced with such a securing means 62. Securing means 62 is implanted by means of a catheter in whose hollow body 63 a pusher 65 is received with axial and torsional mobility. At its proximal end, securing means 62 has a coupling segment 66, which is connected with a coupling receptacle 68 of the pusher with torsional strength but in a detachable manner. Securing means 62 is screwed into the wall of body vessel 1 by a suitable rotary motion of the pusher. As clearly shown in FIG. 9, the torque is transmitted through the mediation of suitable geometries of coupling segment 66 and coupling receptacle 68 in that coupling receptacle 68, with its rectangular cross section, engages coupling segment 66, which is shaped in the form of an elliptic or oval loop.

Figure 10:
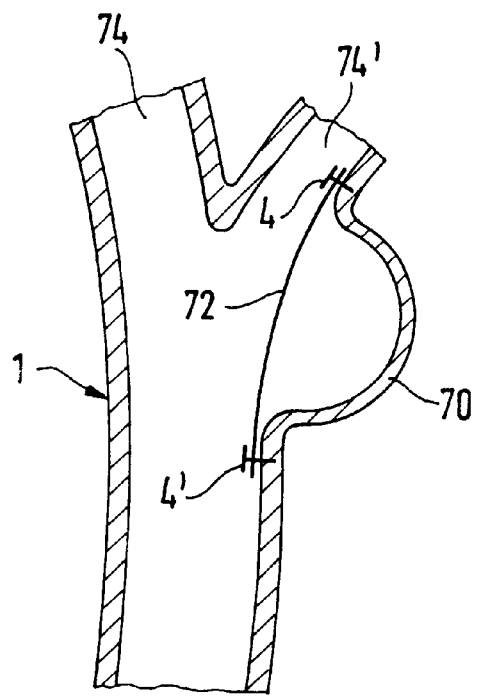
FIG. 10 shows a covering provided for the treatment of an aneurysm, such covering being arranged with securing means on the wall of a body vessel within the region of a branching of the vessel.

FIG. 10 shows a body vessel 1 in the region of a vessel branch, in which a aneurysm 70 has developed. The aneurysm is treated by means of an implantation device as defined by the invention in such a way that a covering 72, which is adapted to the size of the damaged tissue area, and which, for example, may consist of a knitted patch of textile material, a piece of tissue or a patch of plastic, is received in the course of introduction of the implantation device in body vessel 1 in about the region between sleeve 38 and hollow body 36 of a catheter 35, and placed in the site of implantation on the diseased area with the further help of a suitable device, as described in greater detail below. Covering 72 is then tacked to the vascular wall in healthy tissue areas with the help of securing means 4 and 4'.

While with conventional treatment methods, by which, for example, an endoprosthesis adapted to the vascular branch is implanted, Substantial reduction of the cross section of the vessel is unavoidable, and, furthermore, eveil wide healthy areas of the body vessel are jointly treated with rather damaging consequences for such areas, FIG. 10 shows clearly that hardly any segments of body vessel 1 are affected by the therapy beyond the directly damaged region 70, and, furthermore, that a vasoconstriction due to the covering exists only in one of the branches 74, 74' of branching body vessel 1, and even there only to a highly reduced degree as compared to the treatment with a conventional stent.

Figure 11:
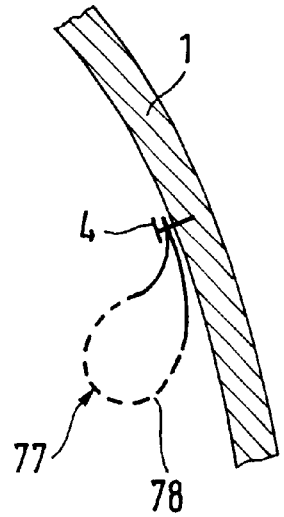
FIG. 11 shows a medication pouch attached to a wall of the vessel with the help of a securing means.

FIG. 11 shows the mounting of a medication-filled pouch 77 with a securing means 4 on vascular wall 1. Pouch 77 has openings 78, through which the medication contained in pouch 77 is dispensed in a controlled manner into the body fluid flowing through body vessel 1. It is especially advantageous if such a pouch 77 is secured within the immediate proximity of a highly localized tissue disease, or in an artery supplying a tumor.

Figure 12:
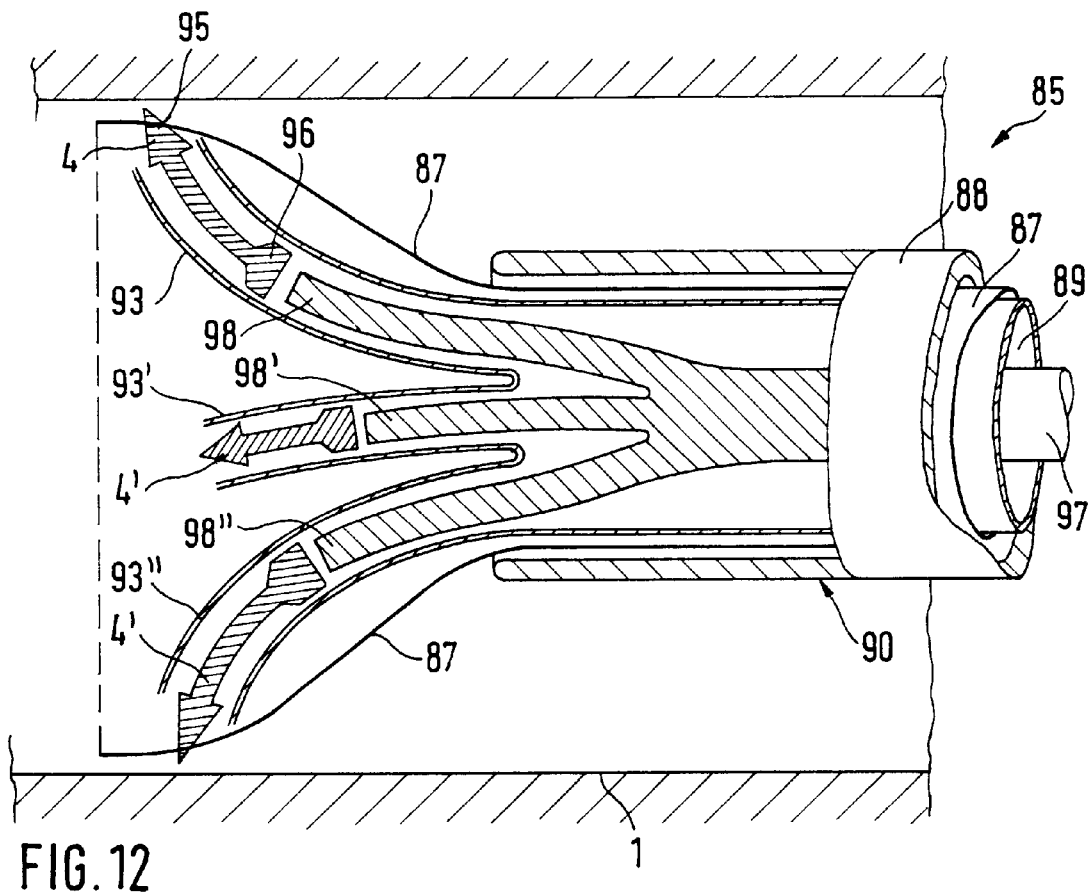
FIG. 12 shows a partly cut view of the front segment of an implantation device of a different design with a plurality of simultaneously implantable securing means.

FIG. 12 shows an implantation device 85 for implanting and securing a hose-like graft 87 in body vessel 1. When implantation device 85 is inserted, graft 87—which preferably consists of an elastic material—is received between a sleeve 88 and hollow body 89 of catheter 90. After catheter 90 has been placed in the correct position, sleeve 88 is retracted by a predetermined distance, whereupon graft 87 expands into its intended implantation position. Such expansion takes place in this connection in such a way that graft 87, which is present in a compressed or folded-in state between sleeve 88 and hollow body 89 of catheter 90 when implantation device 85 is inserted, is released by the retraction of the sleeve and changed into its intended expanded state either automatically or with the help of hollow body 89 of catheter 90.

For said purpose, hollow body 89 has a plurality of receiving sections 93, 93', 93", specifically three in the present exemplified embodiment, which extend parallel with each other when catheter 90 is inserted in body vessel 1, but bent in the implanted state of the catheter in the direction of the wall of body vessel 1, whereby said receiving sections 93, 93', 93" each point in different directions. Receiving sections 93, 93', 93" are bent either by using receiving sections 93, 93', 93" which are designed in the form of curved yet elastic hollow bodies, to begin with, which during the insertion of implantation device 85 are maintained under tension parallel with each other, and automatically bend into their original curved condition upon retraction of sleeve 88. Alternatively, however, a device similar to the one shown in FIG. 5 can be employed, in which filaments are used for bending the receiving sections upwardly.

Securing means 4, 4', 4" are received in receiving sections 93, 93', 93" when catheter 90 is in the insertion condition. The function of said securing means is, on the one hand, to hold graft 87 as catheter 90 is being inserted in body vessel 1, whereby such holding is accomplished in that, for example, the securing means 4, 4', 4" penetrate the graft with part of their implantation segments. On the other hand, securing means 4, 4', 4" serve the purpose of securing graft 87 in its implanted state on the wall of body vessel 1 , which is accomplished in that securing means 4, 4', 4", with their implantation segments 95, penetrate graft 87 and fix the latter on the vascular wall with their holding segments 96. Implantation of securing means 4, 4', 4" takes place in each case by means of a pusher 97 in a manner already known. In the present exemplified embodiment, said pusher is divided at its distal end into a number of front segments 99, 99', 99" corresponding with the number of receiving sections 98, 98', 98", which means that when employed as intended, securing means 4, 4', 4" are simultaneously advanced by such pusher. As an alternative to the branching pusher 97, however, a bundle of pushers—which can be actuated independently of each other—may be arranged in hollow body 88, with each of said pushers serving for implanting one securing means.

Figure 13:
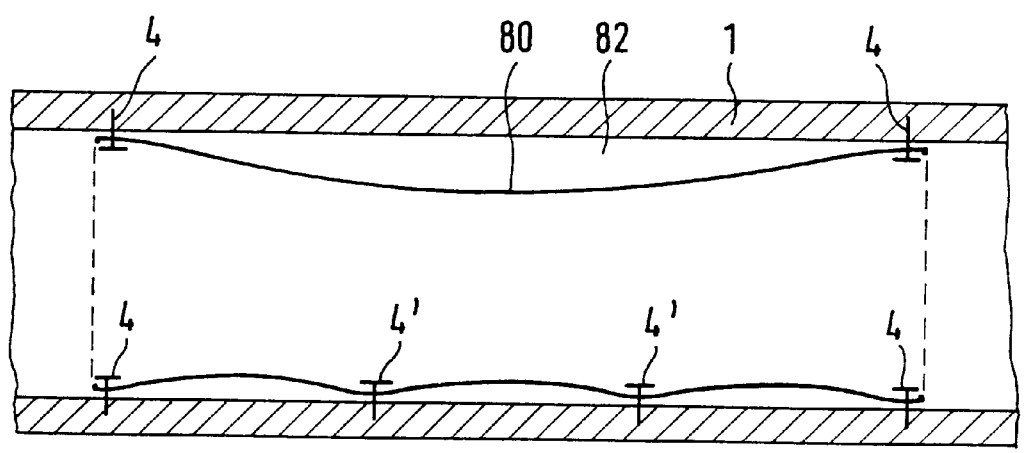
FIG. 13 shows a longitudinal section through a hose-like graft partly tacked with securing means to an inner wall of the vessel, said graft being in its intended condition.

FIG. 13 shows an application possibility for an implantation device as defined by the invention, in which the securing means 4, 4' are employed for securing a hose-like graft 80. Using, for example, the method described above (FIG. 12), the graft is first secured at its distal and proximal ends by means of securing means 4, 4'. Thereafter, however, graft 80 is frequently pulled into the interior of body vessel 1 within the region between the ends due to the suction effect of the body fluid flowing through body vessel 1. This causes the risk of occlusion within region 82 between the stent graft and the wall of body vessel 1. To avoid this, graft 80 is tacked to the wall of body vessel 1 in the region between the ends by means of a suitable number of securing means 4, 4'.

Figure 14:
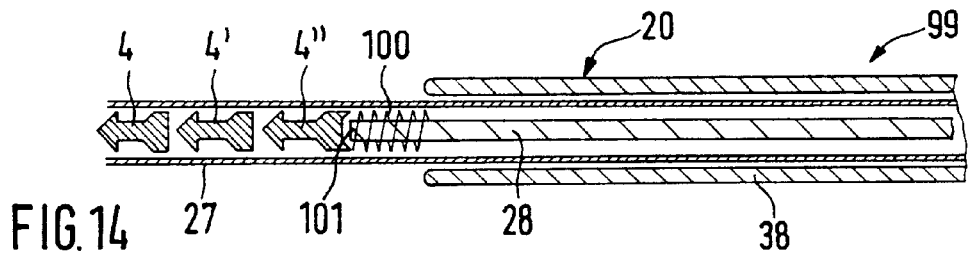
FIG. 14 shows a longitudinal section through an implantation device in the stretched condition, said device being fitted with several securing means and with a spring for supporting the implantation.

Implantation device 99, which is shown in FIG. 14 with a catheter 20 in the stretched state. has a number of securing means intended for sequential implantation, said securing means being arranged one after the other in hollow body 27 of catheter 20. With the present exemplified embodiment, too, hollow body 27 is supported by a sleeve 38 and the securing means are advanced or driven forward with the help of a pusher 28. A coil spring 100 is arranged adjacent to securing means 4", which is disposed closest to pusher 28. When the catheter is inserted, said coil spring is maintained in the tensioned state by a nose 101 projecting on pusher 28. After the intended implantation position of implantation device 99 has been reached, spring 100 is released by turning the pusher, causing the spring to be relieved and to act on the securing means. Securing means 4 is driven in this way into the inner wall of the body vessel.

Figure 15:
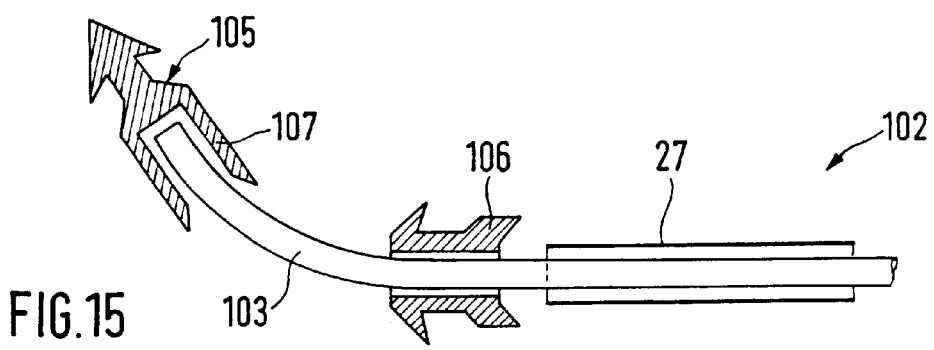
FIG. 15 shows a longitudinal section through a probe in the form of a long-stretched filament for the implantation of securing means and associated securing means.

As opposed to the preceding exemplified embodiments, where the securing means are arranged in the interior of hollow body 27, the hollow body 27 of implantation device 102 shown in FIG. 15 serves for receiving a probe 103 with axial mobility, said probe being designed in the form of a long-stretched filament and being intended for implanting the special securing means 105, 106. Securing means 105 has a rear segment 107 provided with a recess. With said rear segment 107, securing means 105 is received positively locked yet in a detachable manner on the front segment of probe 103. Axial actuation of the probe suffices for implanting securing means 105. On the other hand, however, for implanting securing means 106, which is designed in the form of a hollow element and received with axial mobility on probe 103, hollow body 27 serves as a pusher, which is advanced along probe 103 and in this way advances securing means 106 as well.

Figure 16:
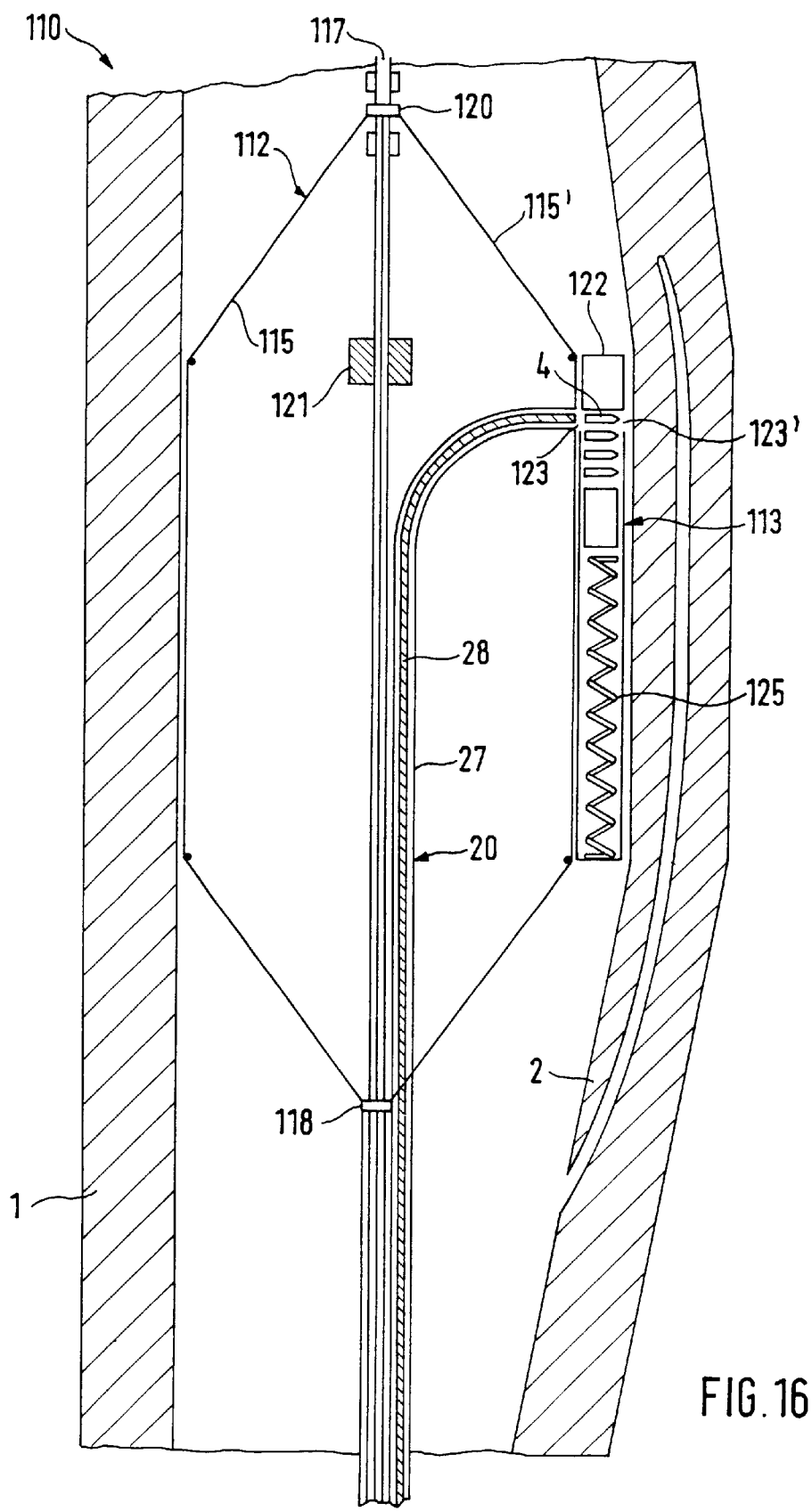
FIG. 16 shows an implantation device received in a vessel (only indicated), said device being provided with a spreading sleeve as well as with a magazine for sequentially implanting securing means.

An implantation device 110 is shown in FIG. 16 in the intended condition for treating a dissecate 2 in a body vessel 1, said implantation device being provided with a spreading sleeve 112 and a magazine 113 for securing means 4.

Spreading sleeve 112 serves for expanding body vessel 1 prior to and during the implantation process. It consists of several bridges 115, 115', which are spaced from each other in the circumferential direction at identical angles. Each of said bridges is structured by three long-stretched segments, which are substantially dimensionally stable and connected with each other in pivot points. A pulling means 120 extending through spreading sleeve 112 and projecting beyond the proximal end 118 of said sleeve is rigidly connected with the distal end 117 of spreading sleeve 112. Bridges 115, 115' are spread by said pulling means in the radial direction by tensile force while spreading sleeve 112 is otherwise held fast. In this way, bridges 115, 115' hold body vessel 1 under the pretension desired for the implantation process.

A magazine 113 is mounted on bridge 115' radially on the outer side. Several securing means 4 intended for sequential implantation are arranged in said magazine along a line next to one another. Casing 122 of magazine 113 has two openings 123, 123' on its front segment, which are aligned with each other and have diameters adapted to the cross section of securing means 4. One securing means is moved into a position between the openings at a time with the help of a spring means 125. Said securing means 4 is implanted in the known manner by actuating a pusher 28, which is guided through hollow body 27 of a catheter 20, said body feeding into opening 123 in the magazine. After the first securing means 4 has been implanted, pusher 28 is retracted from the magazine, whereupon a next securing means 4 is moved by spring means 125 into the starting position suitable for its implantation. An ultrasound probe 121 arranged within spreading sleeve 112 serves for diagnostically monitoring the image of the surgical intervention.

After a securing means 4—which is shown in FIG. 17 again in the form of a spirally wound element as in FIG. 7—has been implanted, implantation device 130 shown in FIG. 17 is capable of placing a next-following securing means 4' in hollow body 27 of catheter 20 without making it necessary to remove catheter 20 from body vessel 1. One or several securing means 4' are arranged in a feeding hose 133, whose lumen is connected with the lumen of hollow body 27, and can be advanced in feeding hose 133 by means of a feeding pusher 134. After securing means 4 has been implanted, implantation pusher 65 is retracted up to beyond the point where feeding hose 133 is connected with hollow body 27. A securing means 4' is subsequently admitted into hollow body 27 with the help of feeding pusher 134. After feeding pusher 134 has been retracted, securing means 4' is available for implantation with the help of implantation pusher 65.

Figure 17:
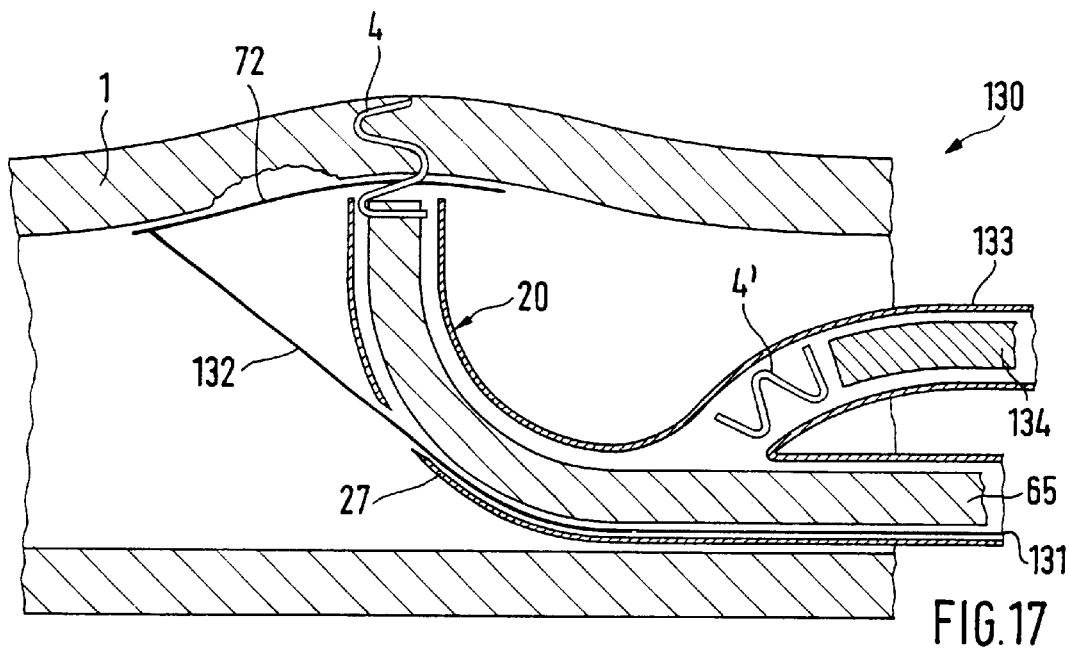
FIG. 17 shows an implantation device received in a vessel, with a feeding hose for inserting securing means.

FIG. 17 also shows a clamping wire 132, which is suitable for mounting a protective covering 72. Clamping wire 132 extends from pusher 65, separated by separation wall 131, through hollow body 27, and is actuated from the proximal end of catheter 20. In the course of implantation, protective covering 72 is pressed against the vascular wall by clamping wire 132 and thus maintained in a correct position as covering 72 is being secured by securing means.

Figure 18:
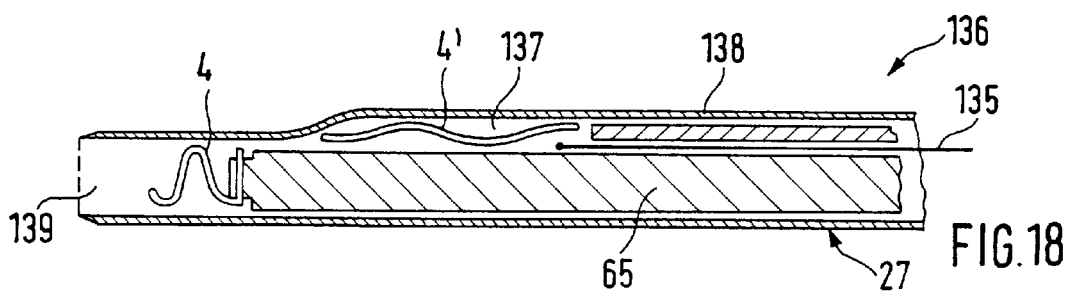
FIG. 18 shows an implantation device with a laterally arranged, elastically stretchable substitute securing means.

FIG. 18 shows yet another embodiment 136 of an implantation device, in connection with which the securing means 4, 4' are made from a highly flexible material. In this embodiment, a securing means 4' is accommodated in a highly stretched condition in a receptacle 137 of hollow body 27 laterally or coaxially relative to implantation pusher 65. In a way similar to the mode of operation of implantation device 130, after securing means 4 has been implanted with device 136, the pusher is retracted to an extent such that securing means 4' can be pushed into the actual implantation channel 139 of hollow body 27 by means of another pusher 138. In said channel, securing means 4' automatically assumes its intended form of implantation and can be implanted by means of implantation pusher 65. In the present embodiment too, implantation channel 135 is separated from receptacle 137 by a separation wall 135, which is interrupted only within the immediate feed zone for securing means 4', thus at the distal end of receptacle 137. Separation wall 135 assures that implantation pusher 65 and feeding pusher 138 do not interfere with each other. Of course, also several securing means 4' may be arranged in receptacle 137 of hollow body 27, disposed one after the other.

Figure 19:
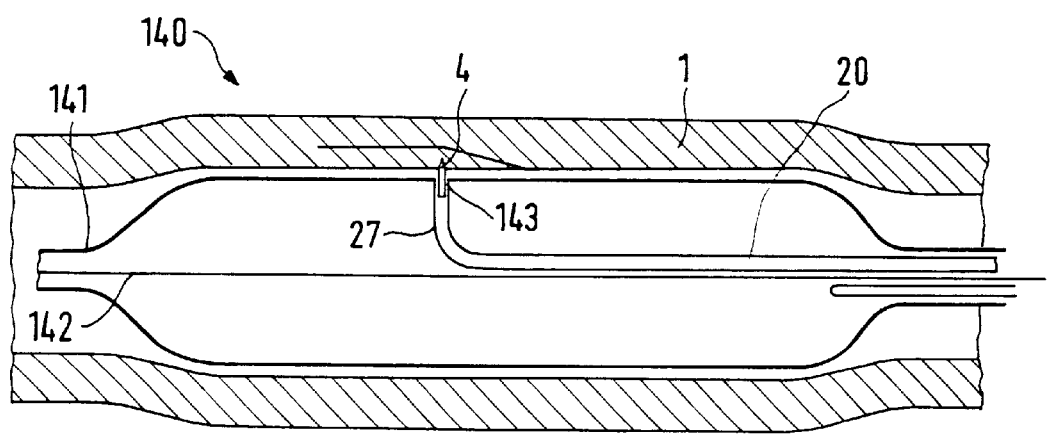
FIG. 19 shows an implantation device arranged in a balloon catheter received in a vessel.

FIG. 19 finally shows an implantation device 140, in which the pretension required for body vessel 1 is produced by means of a balloon catheter 141. Balloon catheter 141 is placed in body vessel 1 with the help of a guide wire 142 and then expanded as intended. Hollow body 27 of implantation catheter 30 partly extends through balloon catheter 141 and feeds into a predetermined opening 143 in the outer shell of balloon catheter 141, from which also securing means 4 is implanted in the vascular wall of body vessel 1 in the manner described in the foregoing.

What is claimed is:

1. An implantation device for the treatment of damaged or tissue within the inner walls of hollow organs, comprising:
   a catheter with a long-stretched hollow body having a closed wall and a lumen, said closed wall being open at least at its front end, said front end being bent upwardly, wherein said front end is tapered to a reduced diameter;
   at least one fastening means loosely accommodated in the hollow body of the catheter, said fastening means having an implantation section, and being accommodated with axial mobility within the hollow body, wherein when said catheter is placed in the organ, said implatation section is implanted in the wall of the hollow organ in a targeted way and subsequently detached from the catheter.

2. The implantation device according to claim 1, wherein the catheter further comprises a protective covering, and means for receiving and positioning said protective covering over diseased tissue, said means being detachable from the catheter upon placement of the catheter in the hollow organ and wherein said means is securable on an inner wall of the hollow organ via at least one of said fastening means.

3. The implantation device according to claim 2, wherein the protective covering is a piece of textile fabric or a porous plastic foil.

4. The implantation device according to claim 3, wherein the protective covering is a hose-like graft.

5. The implantation device according to claim 1, wherein the fastening means is a nail having a shaft, said shaft forming said implantation section.

6. The implantation device according to claim 1, wherein the implantation section is a staple having at least two legs, said legs being arranged in the U- or v-shaped relative to each other.

7. The implantation device according to claim 1, wherein the implantation section comprises at least two elastic legs connected with each other at one end, said legs being arranged substantially in a V-shaped relative to each other.

8. The implantation device according to claim 1, wherein the implantation section of the fastening means is fitted with barbs.

9. The implantation device according to claim 1, wherein the fastening means is made of a biodegradable material.

10. The implantation device according to claim 1, wherein the fastening means comprises an elastic material.

11. The implantation device according to claim 1, wherein the fastening means further comprises a diagnostic contrast medium.

12. The implantation device according to claim 1, wherein the fastening means is adapted to receive and dispense a predetermined amount of medication.

13. The implantation device according to claim 12, wherein the fastening means has a hollow space for receiving the predetermined amount of medication.

14. The implantation device according to claim 13, wherein said fastening means is biodegradable and that the medication is released upon decomposition of the fastening means.

15. The implantation device according to claim 12, further comprising at least one medication pouch connected with a head segment of the fastening means for receiving medications, said pouch having apertures for dispensing the medication at a predetermined release rate.

16. The implantation device according to claim 1, wherein the hollow body of the catheter comprises an elastic material selected from the group consisting of plastic and elastic metal and wherein said front segment is deflectable without changing an inner cross section of said front segment.

17. The implantation device according to claim 1, further comprising a pusher axially removably disposed in said hollow body, said pusher driving the fastening means out of the catheter.

18. The implantation device according to claim 17, wherein the fastening means is designed in the form of a spiral or screw, and when said fastening means is implanted in a vascular wall, said fastening means has an end with a coupling for detachably coupling said fastening means with torsional strength to a corresponding coupling segment of said pusher.

19. The implantation device according to claim 1, wherein the hollow body of the catheter is at least partially received in a sleeve made of elastic material.

20. The implantation device according to claim 1, wherein a front segment of the hollow body is connected with a filament extending with axial mobility substantially across an entire longitudinal expanse of the catheter, said front segment being bendable by means of said filament.

21. The implantation device according to claim 20, wherein the filament extends through a separate lumen in the interior of the hollow body and wherein the front segment of the catheter is bent in the way of a Bowden wire.

22. The implantation device according to claim 1, further comprising a metal reinforcement arranged within a range of deflection of the front segment of the hollow body.

23. The implantation device according to claim 1, further comprising a spring means actively connected to the fastening means for inserting it into the wall of the hollow organ, said spring means being pretensioned as said catheter is inserted but being releasable upon placement of the catheter in the hollow organ.

24. The implantation device according to claim 1, further comprising an electromagnetic drive actively connected with the fastening means for inserting said fastening means into the hollow organ.

25. The implantation device according to claim 1, further comprising an ultrasound arrangement connected with the lumen of the hollow body for supporting insertion of the fastening means into the wall of the hollow organ.

26. The implantation device according to claim 1, wherein there are several simultaneously implantable fastening means received in the hollow body of the catheter.

27. The implantation device according to claim 26, wherein a front segment of the hollow body has a plurality of receiving segments, said receiving segments being arranged parallel with each other as the catheter is being inserted but being bendable in different directions upon placement of the catheter in a hollow organ, each of said receiving segments being adapted for receiving with axial mobility and implanting said fastening means.

28. The implantation device according to claim 1, wherein there are several fastening means arranged one after the other with axial mobility within the catheter for sequential implantation.

29. The implantation device according to claim 28, wherein said fastening means is arranged in a magazine on the catheter, and wherein following each implantation of a securing means, a subsequent fastening means is placed in the hollow body by a loading device for replacing the implanted fastening means.

30. The implantation device according to claim 28, wherein said fastening means is elastically stretchable and arranged with axial mobility in a receptacle of the hollow body, said fastening means being movable into a starting position after implantation of a preceding fastening means via a loading pusher axially movably received in a receptacle.

31. The implantation device according to claim 1, wherein the hollow body of the catheter is connected with a feeding hose for placing the fastening means in the hollow body via a feeding pusher.

32. The implantation device according to claim 1, further comprising a spreading sleeve consisting of bridges separated from each other by longitudinal slits and each being predeflected in an outward direction arranged on the catheter and wherein a pulling element projecting from the distal end of the catheter is solidly connected with said catheter for spreading the bridges by tensile force.

33. The implantation device according to claim 1, wherein the catheter is at least partially received in an interior of a balloon catheter, and wherein the front segment of the hollow body of the catheter is deflectable towards a vascular wall when the balloon catheter is in an inflated state.

34. The implantation device according to claim 1, wherein the hollow body of the catheter is pointed at its front end and is detachably connected with the wall of the hollow organ when the implantation device is implanted.

35. The implantation device according to claim 2, further comprising a plurality of positioning wires for receiving and positioning the protective covering, said wires being received axially movably in corresponding receptacles of the hollow body of the catheter and being actuated independently of each other.

36. The implantation device according to claim 1, wherein said securing means is designed in the form of a hollow element received on a probe consisting of a filament and extending at least by sections coaxially in the catheter, and wherein said catheter is usable as a pusher for the securing means.

37. The implantation device according to claim 1, further comprising a diagnostic ultrasound system actively connected with an image emitter arranged on the catheter for continuously monitoring implantation processes.

* * * * *